United States Patent [19]
Witt

[11] Patent Number: 5,398,667
[45] Date of Patent: Mar. 21, 1995

[54] BACK WARMER

[76] Inventor: Dennis M. Witt, N6 W31967 Shagbark Glen, Delafield, Wis. 53018

[21] Appl. No.: 45,823

[22] Filed: Apr. 9, 1993

[51] Int. Cl.⁶ ............................................. F24J 1/00
[52] U.S. Cl. ................................... 126/263 R; 2/2; 2/44; 126/263 R; 126/204; 126/206
[58] Field of Search ............... 126/263, 204, 206, 400, 126/263 R; 607/112; 224/222; 383/901; D24/206, 207; 2/44, 69, 309, 311, 70, 103

[56] References Cited

U.S. PATENT DOCUMENTS

| | | | |
|---|---|---|---|
| 1,970,081 | 8/1934 | Eisendrath . | |
| 2,573,791 | 11/1951 | Howella | 126/263 |
| 2,612,155 | 9/1952 | Mendez | 126/263 |
| 2,675,798 | 4/1954 | Rosmarin | 126/263 X |
| 2,750,597 | 6/1956 | Blatt | 2/305 |
| 3,476,102 | 11/1969 | Sarnoff | 126/204 |
| 3,980,070 | 9/1976 | Krupa | 126/263 |
| 4,282,005 | 8/1981 | Sato et al. . | |
| 4,527,566 | 7/1985 | Abare | 607/112 |
| 4,604,987 | 8/1986 | Keltner . | |
| 4,688,572 | 8/1987 | Hubbard et al. | 126/204 X |
| 4,756,299 | 7/1988 | Podella . | |
| 4,884,295 | 12/1989 | Cox | 2/2 |
| 4,949,887 | 8/1990 | Holmes . | |
| 4,955,126 | 2/1991 | Matsuda . | |
| 5,046,479 | 9/1991 | Usui | 126/263 X |
| 5,058,563 | 10/1991 | Manker . | |
| 5,060,639 | 10/1971 | Marcus | 2/44 |
| 5,084,986 | 2/1992 | Usui | 126/204 X |
| 5,086,514 | 2/1992 | Ross | 2/2 |

Primary Examiner—Larry Jones
Attorney, Agent, or Firm—Andrus, Sceales, Starke & Sawall

[57] ABSTRACT

A back warmer for keeping a person's lower back warm. The back warmer comprises a flexible pad including an upper panel extending between opposite sides of a person and around a person's lumbar, together with a lower panel extending downwardly from the upper panel to substantially cover a person's tail bone. A belt is formed by a pair of elongate elastic straps attached to opposite sides of the upper panel and extending around a person's waist. The upper panel may also include a pocket for containing a heating element. The back warmer may also include a removable seat cushion extending downwardly from the lower panel which is hinged to the lower panel for use as a stadium cushion or the like.

11 Claims, 2 Drawing Sheets

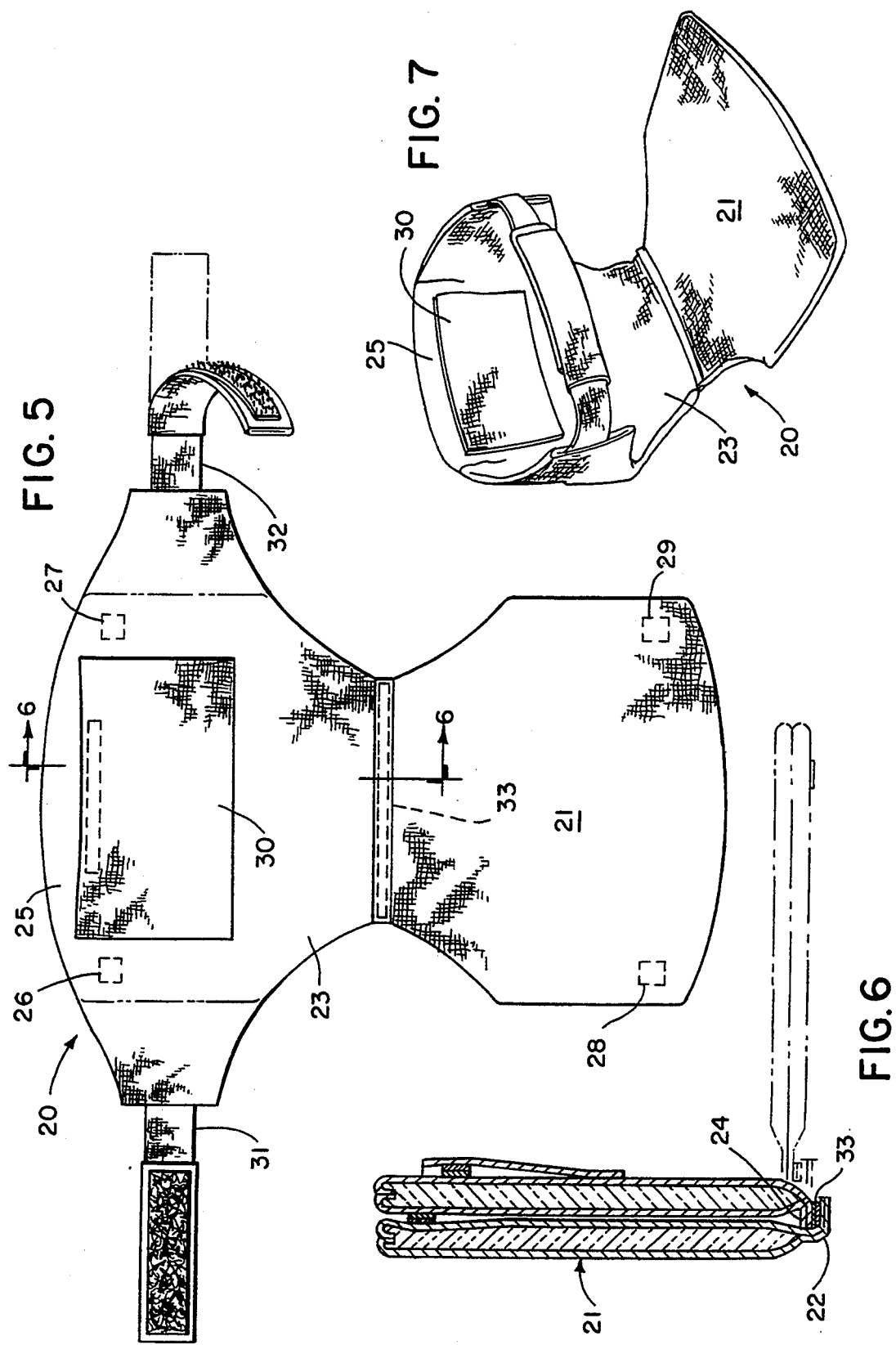

BACK WARMER

BACKGROUND AND SUMMARY OF THE INVENTION

The present invention relates to wearing apparel, and more particularly to a waist encircling wrap for keeping a person's lower back warm.

There are numerous reasons for desiring to maintain a person's lower back warm. For example, persons exposed to cold weather for any extended period of time must be able to retain body heat in order to remain comfortable. In particular, deer hunters or spectators attending an outdoor stadium event need to remain warm since they are exposed to cold weather for extended periods of time.

In order to accomplish this, the present invention provides a flexible pad composed of a material that conforms to the shape of a person's sides and lower back. The pad includes an upper panel extending between opposite sides of a person and around a person's lumbar, and a lower panel extending downwardly from the upper panel to substantially cover a person's tail bone or caudal vertebrae. A belt attached to opposite sides of the upper panel extends around a person's waist for releasably securing the pad to a person's waist. The upper panel may include a pocket adapted to enclose a heating element along with hook and loop fasteners on the upper panel and pocket for closing the pocket and containing the heating element. The pad may also include a removable seat cushion portion extending downwardly from the lower panel which is hinged thereto so that it can be folded up against the outside of the upper and lower panels when not in use.

BRIEF DESCRIPTION OF THE DRAWINGS

The drawings illustrate the best mode presently contemplated of carrying out the invention.

In the drawings:

FIG. 5 is a plan view of a second embodiment of the back warmer;

FIG. 6 is a cross sectional view in elevation of the second embodiment of the back warmer taken along the plane of the line 6—6 in FIG. 5; and FIG. 7 is a perspective view of the back warmer of FIG. 5.

DESCRIPTION OF THE PREFERRED EMBODIMENTS

Figure 1:
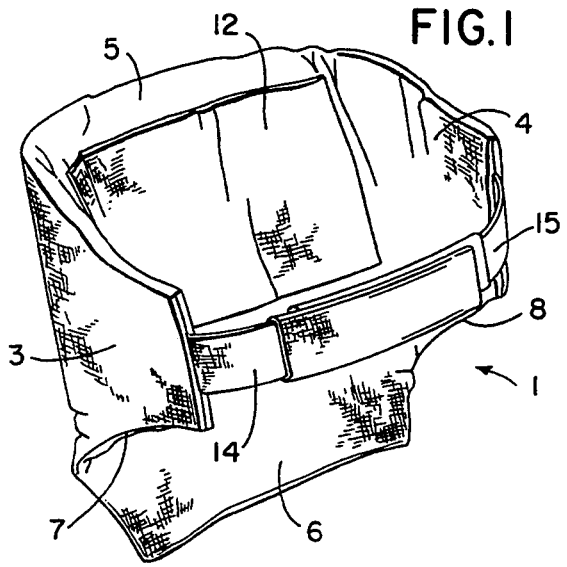
FIG. 1 is a perspective view of a back warmer constructed in accordance with the principles of the present invention.
Figure 2:
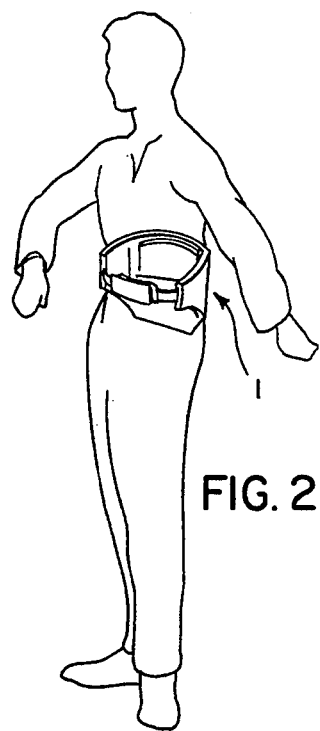
FIG. 2 is a perspective view showing the back warmer strapped to the body of a user.

Referring now to the drawings, FIGS. 1-4 illustrate a first embodiment of a back warmer generally designated by the numeral 1. As shown best in FIG. 2, back warmer 1 is adapted to be worn about the waist of a user and encircles a person's mid section to keep the person's lower back warm.

Back warmer 1 includes a flexible pad composed of a material that conforms to the shape of a person's body. The pad includes an upper panel comprising a central portion 2, a pair of opposite side portions 3 and 4 extending laterally from central portion 2, and an arcuate shaped upper portion 5. As shown best in FIGS. 1 and 2, central portion 2 of the upper panel of the pad covers a person's lumbar region while the side portions 3 and 4 engage opposite sides of a person and upper portion 5 covers or engages a person's lower back. Thus, the upper panel of back warmer 1 extends between opposite sides of a person and around a person's lumbar to cover not only the lumbar but also the person's lower back and sides. Integrally attached to the upper panel of back warmer 1 is a lower panel 6 which extends downwardly from the upper panel to substantially cover a person's tail bone or caudal vertebra. As shown best in FIG. 3, lower panel 6 extends laterally a distance less than the upper panel and is connected to side portions 3 and 4 by arcuate edges 7 and 8.

Figure 4:
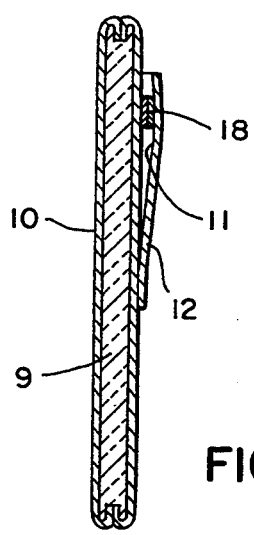
FIG. 4 is a cross sectional view in elevation of the back warmer taken along the plane of the line 4—4 in FIG. 3.

The interior construction of back warmer 1 is best shown in FIG. 4. The upper and lower panels are both composed of an insulating inner material 9 surrounded by a unitary casing 10. Insulating layer 9 is composed of any flexible material commonly used to insulate clothing items, and preferably may be synthetic polyester such as that sold under the trademark "Thinsulate" by the 3M Corporation of Minneapolis, Minn. Insulating layer 9 is contained within casing 10 which is preferably formed of a woven fabric such as wool, but may also be formed from any sheet material such as vinyl, polyethylene or the like. As shown in FIG. 4, casing 10 is sewn along its edges to form a unitary structure.

Figure 3:
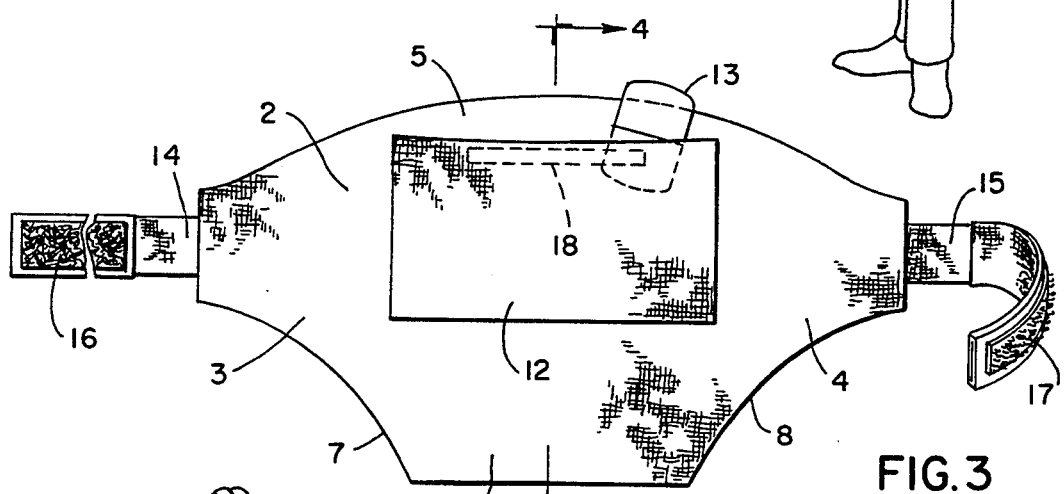
FIG. 3 is a plan view of the back warmer.

As shown best in FIGS. 3 and 4, the upper panel of back warmer 1 includes a pocket 11 formed by a pocket forming panel 12 for holding a chemical heating element 13. Panel 12 is sewn along its lower and side edges to form pocket 11, and includes a means for closing pocket 11 along its top edge. This closure means is preferably a hook and loop fastener 18 for closing the pocket 11 and containing the heating element 13 therein.

Heating element 13 may be any device which generates substantial heat by means of a chemical reaction, but preferably comprises a solid granular material which generates an exothermic reaction on exposure to air. Typically, such a device comprises finely divided elemental iron and certain salts packaged in an air permeable enclosure. The granular materials are packaged in an air permeable packet which is enclosed in an air tight plastic envelope. When the envelope is removed and the packet is exposed to air, the oxidation of the iron produces a steady heat at about 130° to 150° F. for 5-7 hours. If the packet is replaced in the air tight envelope during its useful life, the reaction stops and will restart on reexposure to air.

Back warmer 1 also includes a belt for attachment to a person's waist. As shown best in FIGS. 1 and 3, the belt comprises a first elongate elastic strap 14 having its inner end attached to side portion 3 of the upper panel, and a second elongate elastic strap 15 having its inner end attached to the opposite side portion 4 of the upper panel. The free ends of straps 14 and 15 include interengaging fastening means for releasably fastening the outer ends of straps 14 and 15 together. Preferably, this interengaging fastening means comprises hook and loop fasteners 16 and 17. It should be noted that although the various fastening means, namely elements 18, 16 and 17 have been shown to be conventional hook and loop couplers, any interengaging fastening means may be used to attach the various components of the back warmer together. Particularly preferred interengaging fastening means are the hook and loop fasteners available under the trademark "Velcro" which are widely used commercially and which consist of patches of hooks and loops which interconnect when pressed together but which will be easily pulled apart. Such fasteners have all the advantages of an adhesive, but selectively adhere only to each other and do not adhere to other surfaces. Therefore, such fastening means is ideally suited for articles of apparel such as back warmer 1.

Referring now to FIGS. 5–7, there is illustrated a second embodiment of a back warmer generally designated by the numeral 20. As shown, back warmer 20 includes an upper panel 25, lower panel 23, pocket 30 and straps 31 and 32 identical to those described with respect to the back warmer 1 of FIGS. 1–4. Accordingly, a detailed description thereof has already been provided. However, in this second embodiment, there is further included a seat cushion portion 21 extending downwardly from lower panel 23. The upper edge of seat portion 21 is releasably fastened or secured to the lower edge of the lower panel 23 so that portion 21 can be easily removed if desired. As shown best in FIG. 6, this releasable fastening or securing means is preferably hook and loop fastener means 33 such as "Velcro". As shown best in FIG. 6, the upper edge of portion 21 includes a strip 22, and the lower edge of the lower panel 23 includes a complementary strip 24 which mounts the hook and loop fastener means 33. Additionally, strips 22 and 24 also provide a hinge enabling seat cushion portion 21 to be folded upwardly behind lower panel 23 and upper panel 25. Again, an interengaging fastening means is utilized to fix seat cushion portion 21 to the outer surface of upper panel 25 as shown by hook and loop fastener members 26–29. Thus, when not in use, seat cushion portion 21 is folded up behind panels 23 and 25 and fastened thereto as shown in solid lines in FIG. 6. However, when in use, seat cushion portion 21 is disengaged from panel 25 and folded downwardly into the position shown in phantom lines in FIG. 6 and in full lines in FIG. 7. Also, as noted above, seat cushion portion 21 can be completely removed from back warmer 20 if desired.

Various modes of carrying out the invention are contemplated as being within the scope of the following claims particularly pointing out and distinctly claiming the subject matter regarded as the invention.

I claim:

1. A back warmer and insulating garment for keeping a person's lower back warm, comprising:
    a flexible, insulating pad conforming to the shape of a person's torso including an upper panel having an arcuate shaped portion extending upwardly to substantially cover a person's lower back and extending between opposite sides of a person and around a person's lumbar and having opposite side portions encircling a person's waist, and a lower panel extending laterally a distance less than said upper panel and downwardly from said upper panel to substantially cover a person's caudal vertebra, said lower panel having arcuate edges connected to said side portions; and
    belt means attached to said opposite side portions of said upper panel and extending around a person's waist for releasably securing said pad to a person's waist.

2. The back warmer of claim 1 wherein said belt means comprises a first elongate elastic strap having one end thereof attached to one side of said upper panel, a second elongate elastic strap having one end thereof attached to the opposite side of said upper panel, and interengaging fastening means fixed to the other ends of said first and second straps for releasably fastening said other ends together.

3. The back warmer of claim 2 wherein said interengaging fastening means comprises hook and loop fasteners.

4. The back warmer of claim 1 wherein said upper and lower panels are of a one-piece construction composed of an inner lining and an outer casing.

5. The back warmer of claim 4 wherein said outer casing is composed of a woven cloth, and said inner lining is composed of a heat insulating material.

6. The back warmer of claim 1 further including a pocket formed on said upper panel adapted to enclose a heating element.

7. The back warmer of claim 6 further including hook and loop fastener means on said upper panel and pocket for closing said pocket and containing said heating element therein.

8. A back warmer and insulating garment for keeping a person's lower back warm, comprising:
    a flexible insulating pad conforming to the shape of a person's torso including an upper panel extending between opposite sides of a person and around a person's lumbar, and having opposite side portions encircling a person's waist and a lower panel extending downwardly from said upper panel to substantially cover a person's caudal vertebra;
    belt means attached to said opposite side portions of said upper panel and extending around a person's waist for releasably securing said pad to a person's waist; and
    a seat cushion portion extending downwardly from said lower panel, and hinge means for hingedly connecting said seat cushion portion to said lower panel.

9. The back warmer of claim 8 further including hook and loop fastener means on said seat cushion portion and said upper panel for releasably fastening said seat cushion portion to said upper panel.

10. The back warmer of claim 8 further including securing means for releasably securing said seat cushion portion to said lower panel.

11. The back warmer of claim 10, wherein said securing means comprises hook and loop fastener means on said lower panel and said seat cushion portion.

* * * * *